United States Patent [19]
Nerli

[11] Patent Number: 5,858,225
[45] Date of Patent: Jan. 12, 1999

[54] DENTAL FILTER WITH SANITARY HANDLING

[76] Inventor: Robert A. Nerli, 1370 Hayne Rd., Hillsborough, Calif. 94010

[21] Appl. No.: 843,216

[22] Filed: Apr. 14, 1997

[51] Int. Cl.$^6$ .................................................. B01D 17/038
[52] U.S. Cl. ....................... 210/232; 210/167; 210/416.1; 210/435; 210/441; 210/444; 210/DIG. 17; 433/97
[58] Field of Search ..................................... 210/232, 167, 210/416, 435, 441, 444, DIG. 17, 440, 442, 443; 433/97

[56] References Cited

U.S. PATENT DOCUMENTS

| 5,407,565 | 4/1995 | Austin, Jr. et al. ..................... 210/232 |
| 5,571,412 | 11/1996 | Nerli . |

*Primary Examiner*—David A. Reifsnyder
*Attorney, Agent, or Firm*—Thomas M. Freiburger

[57] ABSTRACT

A filter canister assembly for receiving waste from a dental cuspidor includes a canister of generally conventional configuration, with an open upper end fitted with a canister closure, the canister containing a closed disposable filter basket. A hand grip on the closed filter allows a dental technician to hold and dispose of the filter basket without contacting waste material contained within the filter.

9 Claims, 5 Drawing Sheets

DENTAL FILTER WITH SANITARY HANDLING

SPECIFICATION

BACKGROUND OF THE INVENTION

The invention relates to dental equipment, and more specifically the invention is concerned with a changeable filter for a dental cuspidor. This invention includes modifications and improvements over the filter assemblies described in U.S. Pat. No. 5,571,412, which is hereby incorporated by reference.

Cuspidors for dental operatories are typically fitted with a filter assembly connected to receive the effluent waste (which includes blood and saliva from the dentist's patients) from the cuspidor. The filter typically has a plastic perforated filter screen, designed to remove most solids of significant size, along with blood and other materials associated with the solids. These solids include large particles of amalgam (containing mercury), and the filter prevents them from entering the sewage system. The filter element, generally a basket-shaped element, is usually removed and changed frequently. Originally, cuspidor filters were not disposable and had to be removed and cleaned. More recently, the filter element has been disposable and need not be cleaned, but the task of changing the filter has been one of the most undesirable, distasteful jobs in the dental office, with a great possibility of cross infection, or infecting of the dental office staff.

A conventional filter canister has a canister body, and a lid or cover under which the filter basket is contained. The material from the cuspidor enters the filter canister from below, through one or several inlet tubes, passes through the filter and is discharged through an exit tube at the bottom of the canister, generally drawn by a vacuum.

A conventional dental cuspidor filter canister is formed of a relatively tough but flexible plastic material which is integrally molded to include at least two tube connecting nipples at its bottom side, at least one for entry of liquid and solid material from the cuspidor, and at least one for the filtrate outlet. The canister has a generally cylindrical chamber which receives a basket shaped disposable filter to be dropped in from above. The inlet opening, or, as typically provided, the two inlet openings, have cylindrical collar extensions extending upwardly and vertically disposed inside the chamber, and the filter basket has similarly positioned cylindrical collars which slide down over and fit fairly closely on the inlet collars of the canister. Thus, with the filter basket in place, liquids entering the inlet or inlets will flow up through the filter basket collars and pour out into the canister plenum above the filter mesh, which is at the bottom of the filter basket.

When fully installed, the filter basket sits at a slightly elevated position above the bottom of the canister, such that a small space, e.g. about ¼ inch, is defined below the filter mesh and above the interior bottom of the canister. This space collects filtrate for exiting through the outlet in the bottom of the canister.

A vertical stem or post typically is formed integrally with the disposable filter basket, positioned in the center of the basket and being the uppermost extension of the filter basket. This stem enables gripping between the thumb and finger of the attendant, for removal and changing of the filter basket. Normally the stem is covered with cuspidor effluent.

At the top of the canister, a cover or lid of similar plastic to that of the canister is provided, often having some form of locking engagement device for securing to the canister, which may require placing the lid on the canister at a certain orientation followed by rotation to lock the lid in place. An O-ring may be included on the lid for sealing against a rim surface on the canister.

It is among the objects of the present invention to make easier and more efficient, and particularly to make less distasteful and safer, relative to cross-contamination and infection of dental staff, the task of changing the filter in a dental cuspidor filter assembly. A further object is to provide a filter structure which allows material (waste) to be disposed of into a waste disposal container, in a contained environment.

SUMMARY OF THE INVENTION

In accordance with the present invention, a filter canister for a dental cuspidor contains a disposable, closed filter basket. In a preferred embodiment the filter basket fits into an existing conventional filter canister, and has a hand gripping means at its top which enables a user to remove and dispose of the filter basket without contacting waste material contained within the filter basket.

Thus, in one preferred embodiment a filter canister for a dental cuspidor filter assembly includes a container of conventional configuration, generally defining a closed volume, with an outlet in the container communicating with the closed volume and comprising an outlet tube or nipple for connection to a source of suction to be applied to the filter canister. At least one inlet tube communicates with the interior of the closed volume of the canister, for delivering waste material from the cuspidor to be filtered. The canister has a closure or lid with means for engagement directly with the canister and for providing a seal with the canister when engaged with the open end. Positioned within the canister is a disposable filter basket, positioned when installed in the canister so as to receive suction from the outlet tube against an outlet side of the filter and to receive waste material from the inlet tube at an inlet side of the filter. The filter basket has a lid secured thereto and covering the basket, having a hand gripping means on its top exterior surface. The hand grip allows a user to handle the filter basket without contacting waste material contained within the filter. Thus, the filter of the dental filter canister can be quickly and sanitarily changed by removal of the canister closure, removal of the closed filter basket by the user's grabbing the hand gripping means, disposal of the filter basket, replacement with a similar new disposable closed filter basket and replacement of the canister lid.

It is therefore the main object of this invention to make more sanitary the task of changing the filter in a dental cuspidor filter assembly, specifically by providing a closed, disposable filter basket with a grippable top isolated from the contaminants, eliminating contaminating contact. These and other objects, advantages and features of the invention will be apparent from the following description of a preferred embodiment, considered along with the accompanying drawings.

DESCRIPTION OF PREFERRED EMBODIMENTS

Figure 1:
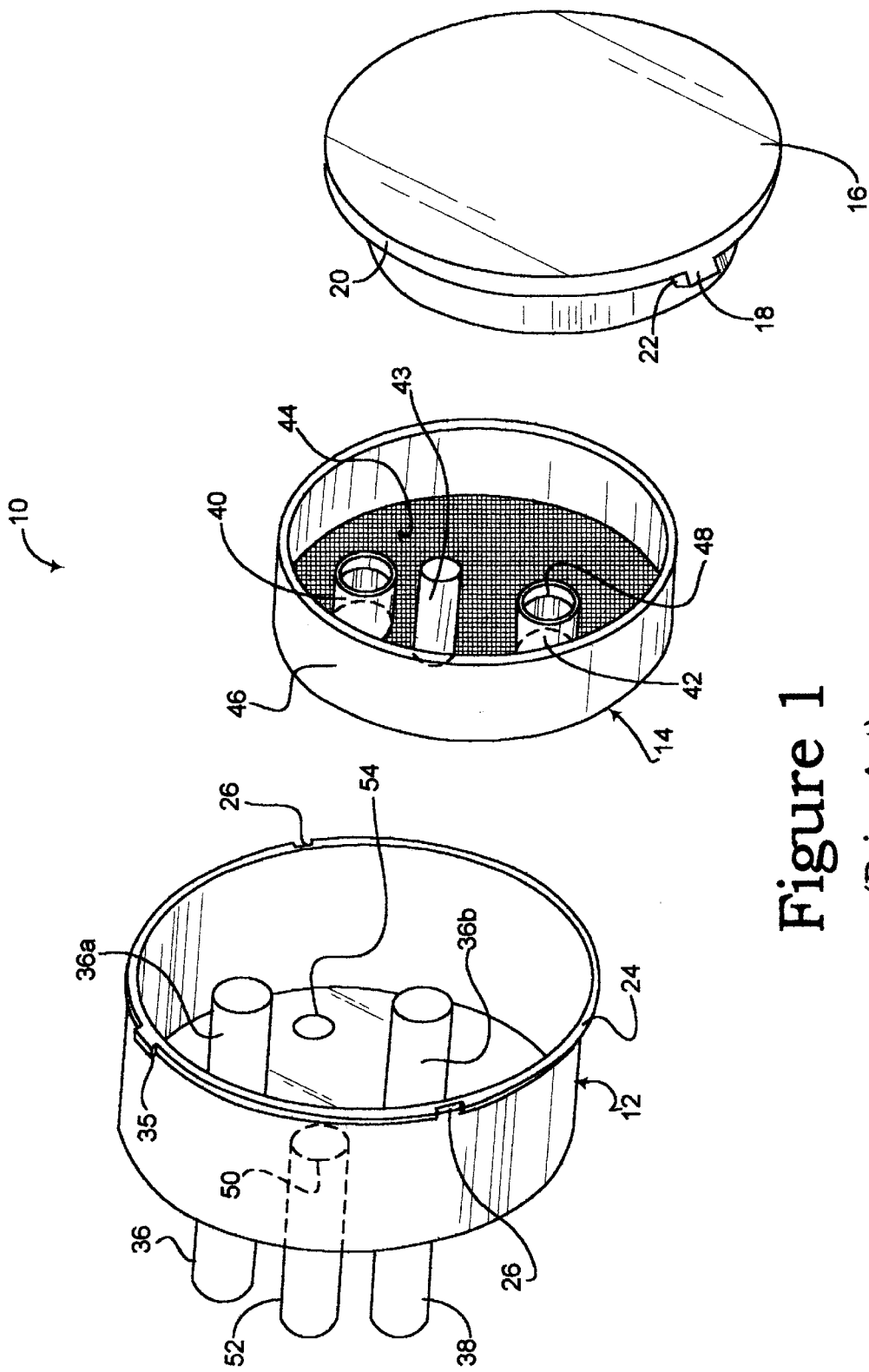
FIG. 1 is an exploded perspective view showing a dental cuspidor filter assembly in accordance with the prior art, including a canister, a filter basket and a covering lid.

In the drawings, FIG. 1 shows a dental cuspidor effluent filter assembly 10 in a configuration which is typical of the prior art. The filter assembly 10 includes a molded plastic canister 12 (e.g. of rigid molded plastic or metal), a replaceable filter basket 14 (which may be of polyethylene, for example) and a covering lid 16. As can be seen from the exploded view of FIG. 1, the lid of the prior art filter assembly is retained to the canister by a pair of depending tabs 18 extending down from a lip 20 of the lid, each tab being generally hook shaped, with an inwardly extending nipple 22. This pair of tabs 18 requires the lid to be oriented at a prescribed rotational position to enable securing of the lid down onto a top lip 24 of the canister. At that point, the nipples 22 have passed through notches 26 in the upper lip and are below the level of the upper lip of the canister. Thus, the lid can be rotated to a locking position wherein the tab nipples 22 are tightly retained under the upper lip 24 of the canister. The canister covering lid typically includes an O-ring (not shown) in a recess in the underside of the closure lid. The O-ring is tightly engaged against the surface of the upper lip 24 when the lid has been installed and rotated to the locked position. The locked position may be defined by one or a pair of stops 35 on the periphery of the canister, as shown. Some conventional filter canisters had an O-ring but no locking feature, and the suction within the canister held a seal at the O-ring. Some had neither locking feature nor O-ring.

As also shown in the prior art drawing of FIG. 1, the canister 12 has a series of openings at its bottom side, comprising inlets and outlets for the filter assembly. A pair of integrally molded depending tubes 36 and 38 preferably are provided, for parallel inflow of fluids from the cuspidor to be filtered. At the interior of the canister these tubes continue, extending upwardly as collar extensions 36a and 36b as shown, so that the filtered material is received into the canister at an elevated position. As seen in the drawing, the filter basket 14 has a pair of similar but larger-diameter tubes or collars 40 and 42, which slide down over the interior canister uprights or collars 36a and 36b.

A lifting stem or post 43 extends up from the bottom of the filter basket to enable removal of the basket.

The filter basket has a perforated bottom 44 for the filtration function, with a peripheral annular wall 46 extending up from the periphery of the bottom. The tubular uprights or collars 40 and 42 in the filter basket have stops 48 comprising an internal diameter reduction, for the purpose of holding the filter basket at a somewhat elevated position above the bottom of the canister. Thus, the filtrate from the filter basket has a plenum below the basket in which to collect. The filtrate exits the filter canister through an outlet opening 50, again with a tubular collar 52 for connection of a transfer conduit tube (not shown) which is a high volume suction line. This aids in the filtration function by applying a negative pressure below the filter basket. An additional opening 54 and tube connection collar (not shown) depending from the bottom of the canister may be provided for various types of cuspidor systems well known in the dental field.

Figure 2:
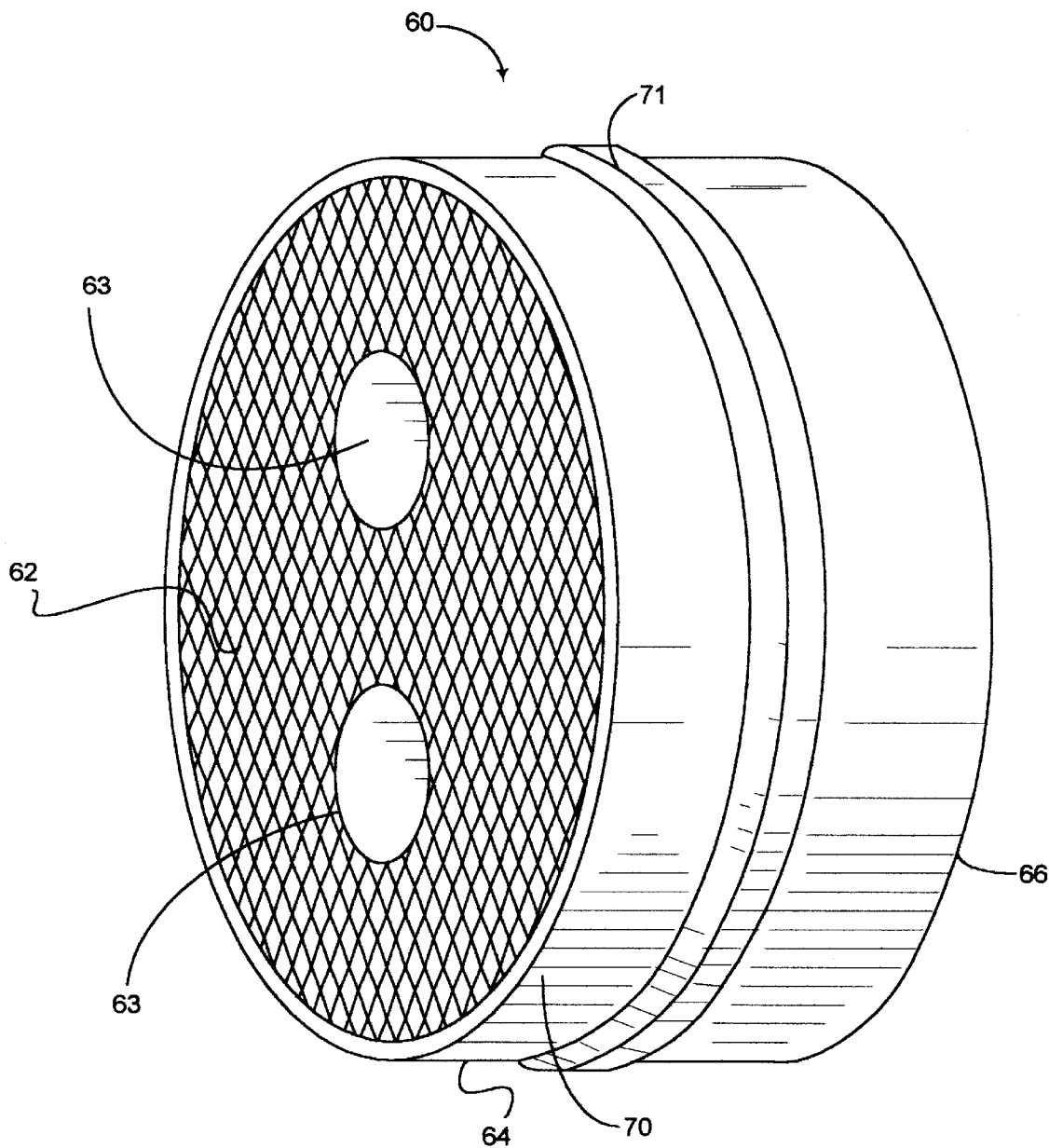
FIG. 2 is a perspective view showing a dental cuspidor filter basket according to the present invention.
Figure 3:
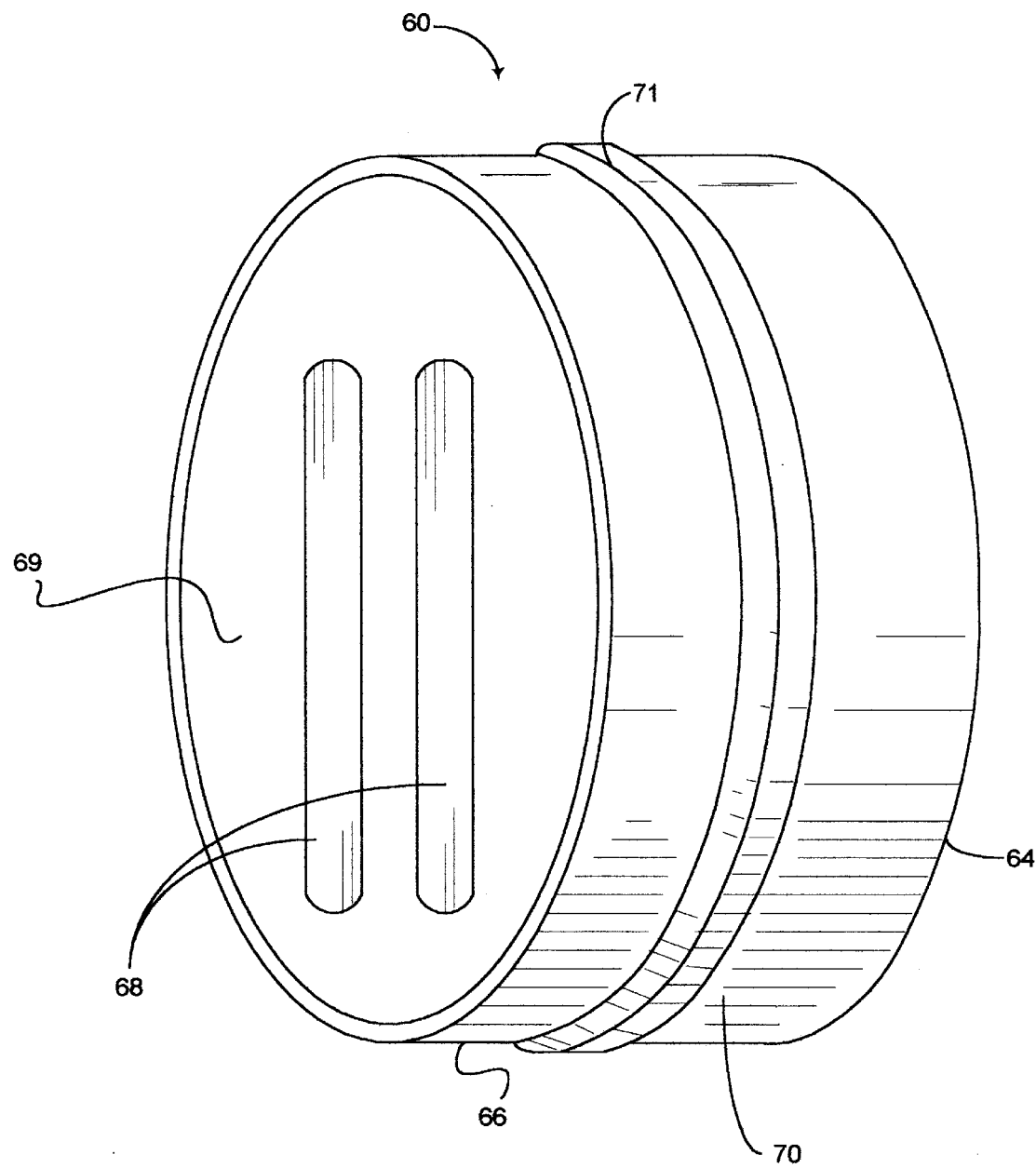
FIG. 3 is another perspective view from the opposite end as that of FIG. 2, showing the dental cuspidor filter basket.

FIGS. 2 and 3 show a dental cuspidor filter/basket 60 of the present invention. The canister which receives the filter basket 60 preferably is identical to the conventional canister described above and shown in FIG. 1, so that the invention can be used directly with the existing dental filter assembly in the dentist's office.

Figure 4:
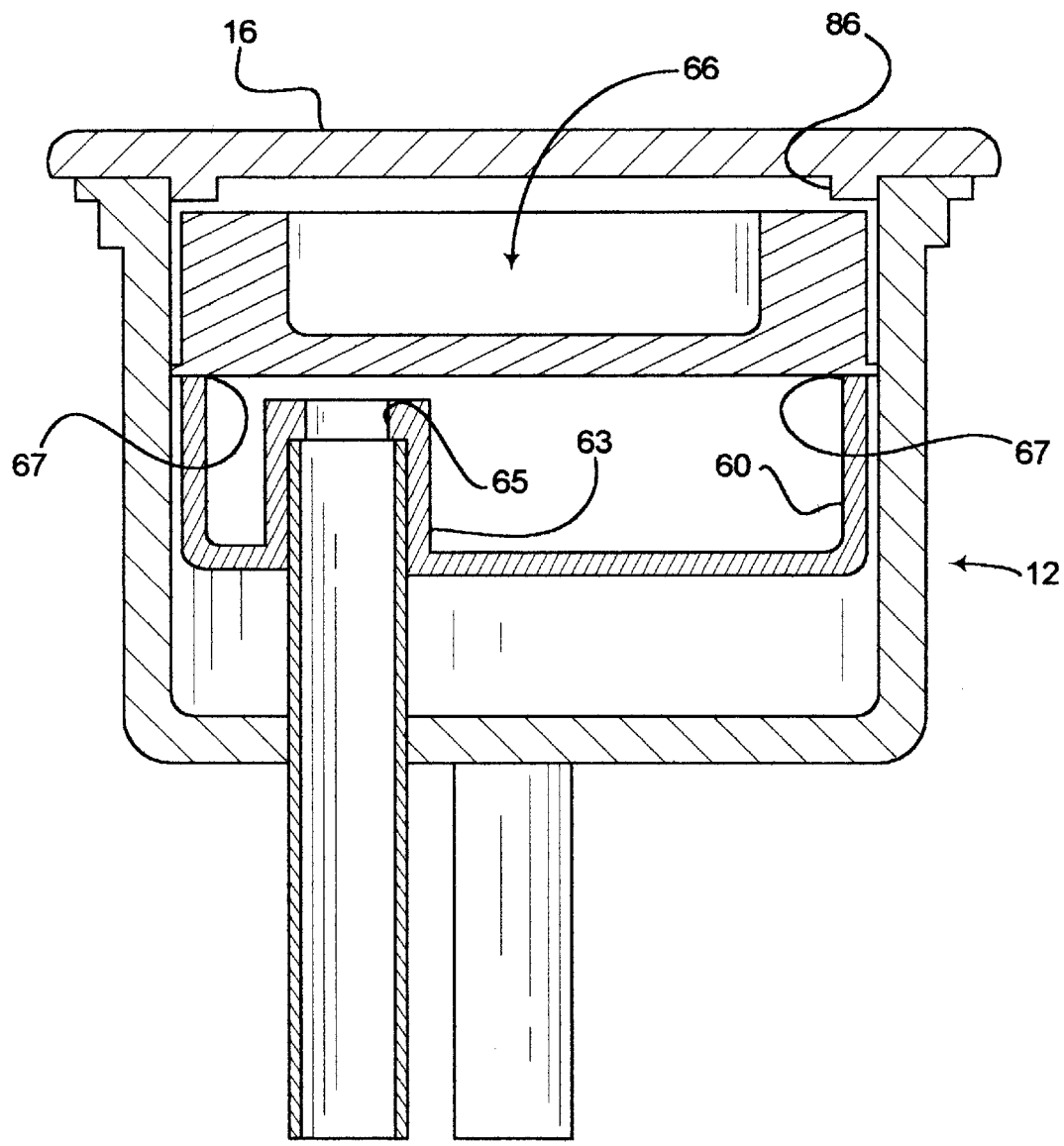
FIG. 4 is a sectional view showing the filter basket assembly of the invention as contained within a filter canister.

In one specific embodiment the filter basket 60 is formed of two assembled components, a basket bottom 64 and a filter closure 66 having a lip 71, with the components preferably snapped together. The components may be permanently secured together, such as by a permanent adhesive or by heat bonding. FIG. 4 shows the lid 66 bonded to the lower basket portion 64 at an upper edge 67 of the basket portion 64. Both of these components are preferably designed to be disposable, so that when the filter basket is removed from the canister 12, the entire assembly 60 is discarded and another is put in its place. One reason the snapped-together embodiment may be preferred is to enable retrieval of anything of value which might go into the filter basket.

A gripping device 68 preferably is provided in the top exterior surface of the filter basket's closure, and this may comprise two parallel indentations formed in the closure, with a bar 69 between the indentations. A user can hold the filter basket by the hand grip, thus eliminating any contact with the waste material contained within the filter basket.

Other forms of hand grip may be used in lieu of that shown. For example, the closure or lid may be a thinner, flat cover bonded to the top edge of the lower basket portion but having a simple gripping stem extending up from generally the center of the lid. The hand grip is preferred, but could be eliminated (the used filter could be retrieved by a tool or suction cup, for example).

The basket 60 has a perforated bottom 62 which may be generally flat as shown in FIG. 2. The perforated bottom may be molded as a matrix of perpendicular bars or lines, forming generally square holes between them (detail not shown), or it may be formed with round holes. As shown in the drawings, a pair of upright tubular collars 63 are integrally formed with the bottom 62 and extend upwardly therefrom. These tubular collars are designed and positioned so as to slide down over the canister tubes or collars 40 (FIG. 1) as in the prior art. As seen in FIG. 4, the tubular uprights or collars 63 in the filter basket have stops 65 comprising an internal diameter reduction, for the purpose of holding the filter basket at a somewhat elevated position above the bottom of the canister. Thus, the filtrate from the filter basket has a plenum below the basket in which to collect.

Figure 5:
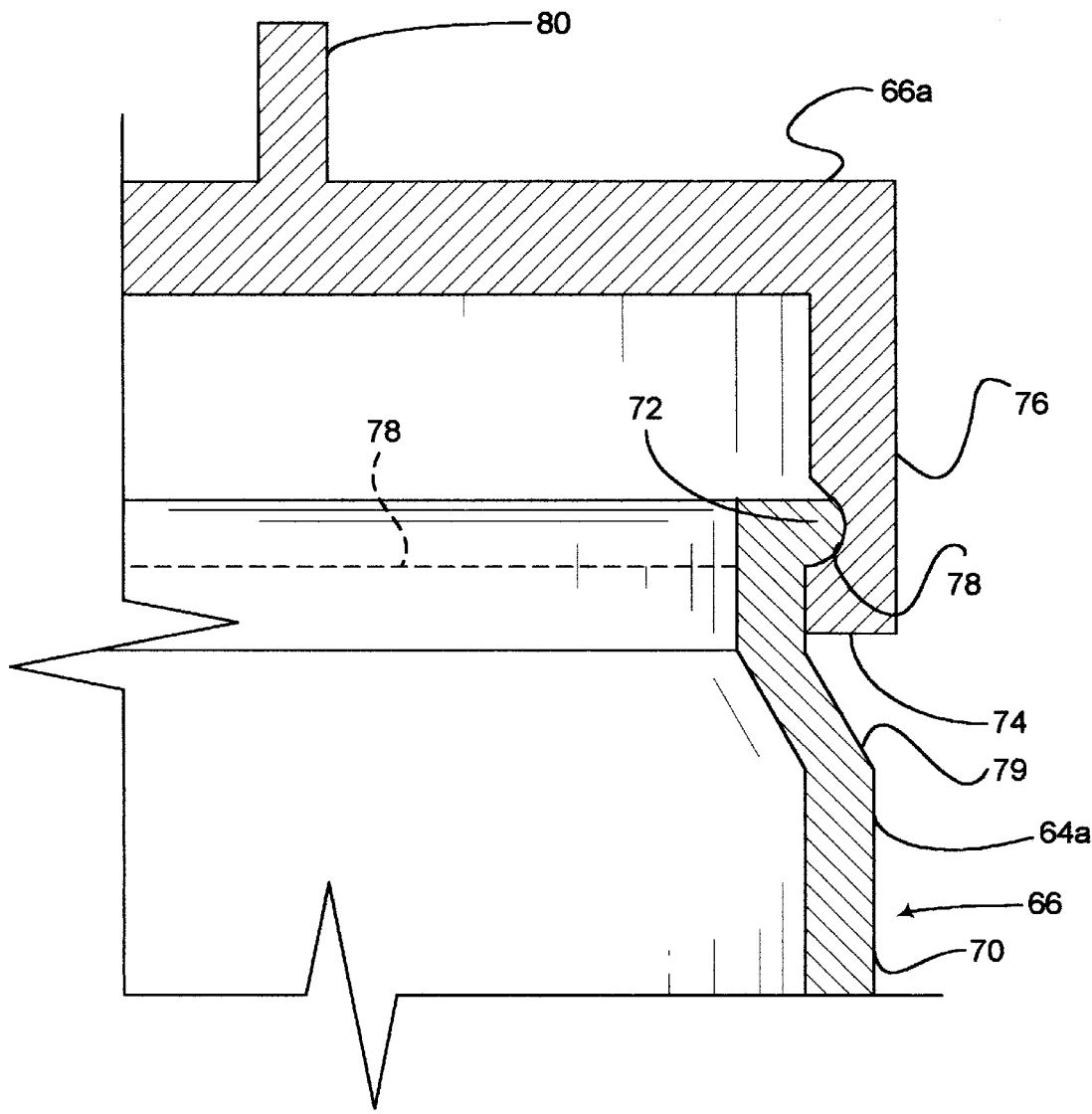
FIG. 5 is an enlarged detail sectional elevation view showing a part of the filter basket assembly, and showing one form of closure connection comprising a snap fit connection arrangement retaining the closure to the filter basket bottom.

In a preferred embodiment, seen in FIG. 5, a snap together arrangement may be used to secure the filter closure 66a to the filter bottom 64a. In the arrangement shown, the filter bottom 64 has an annular outer peripheral wall 70 which is generally the same as that of the conventional configuration described above, but with an outwardly extending lip 72 which will snap together with the filter closure 66a by being forced within the slightly smaller-diameter annulus of an inwardly extending bump or lip 74 on a downwardly extending cylindrical collar 76 of the closure 66, and preferably into an annular groove 78. The wall 70 may angle inwardly as shown at 79 so that the components fit the conventional canister's interior.

FIG. 5 also shows a simple stem 80 integral with the closure 66a and extending up as a hand grip for convenient handling of the disposable filter basket.

The closure or covering lid 66a may be formed of clear polypropylene, low-density polyethylene or similar plastic material which may be semi-rigid or flexible.

As shown in the drawing figures, the contaminated lifting stem 43 of the conventional, open-topped filter basket described above (and shown in FIG. 1) is eliminated in the closed filter basket assembly 60 of the invention. Instead of the lifting the filter basket by such an internal lifting stem, the dental technician simply lifts the filter basket by gripping the hand gripping device on the outside of the basket closure, whether it is the grip 68, 69 of FIGS. 3 and 4 or the grip 80 of FIG. 5. Thus, removal of the filter basket is a much more sanitary procedure.

As noted above, the filter basket lid connection may be permanent, and this may be accomplished, for example, heat sealing, sonic bonding, adhesive or solvent bonding or other appropriate securing means.

Referring to FIG. 4, the lid 16 of the canister assembly simply seats into the rim of the canister 12 as in the prior art.

Also as in the prior art, when a new filter basket is to be placed in the filter canister, the canister cover 16 is removed, the used basket is removed and a new filter basket 60 is simply lowered part way into the canister and rotated until the inlet tubes and collars line up, allowing the filter basket 60 to be pushed the remaining distance into place. The difference is that the filter basket of the invention is closed at the top and handled more safely.

The above described preferred embodiments are intended to illustrate the principles of the invention but without limiting its scope. Other embodiments and variations to these preferred embodiments will be apparent to those skilled in the art and may be made without departing from the essence and scope of the invention as defined in the claims.

I claim:

1. A filter canister assembly for receiving and filtering waste from a dental cuspidor, comprising:

a canister generally defining an internal chamber and having an open end, an outlet means, connected to the canister and in fluid communication with the internal chamber, for connection to a source of suction to be applied to the canister, inlet means in fluid communication with the interior of the chamber of the canister, for delivering waste material from said cuspidor, to be filtered, a canister closure fitted to the open end of the canister, and a disposable filter basket fitted into the internal chamber of the canister via said open end, having side walls, a perforated bottom end comprising a filter screen, and a filter closure secured to the side walls of the filter basket so as to close an upper side of the filter basket, the filter basket being positioned in the canister's internal chamber so as to receive suction from the outlet means against an outlet side of the filter screen and to receive waste material from the inlet means at an opposite, inlet side of the filter screen, whereby the disposable filter basket of the filter canister can be quickly changed by removal of the canister closure, removal and disposal of the closed filter basket, replacement with another disposable filter basket and replacement of the canister closure.

2. The filter canister assembly of claim 1, wherein the filter closure has hand gripping means on its exterior top surface.

3. The filter canister assembly of claim 2, wherein the hand gripping means includes two downward indentations defining a bar between the indentations, whereby an operator may remove the filter basket from the canister without contacting waste material within the filter basket by holding the filter basket by the hand gripping means.

4. The filter canister assembly of claim 2, wherein the inlet means of the canister includes at least one generally cylindrical tube extending into the canister, and wherein the filter basket includes at least one inlet opening in the perforated end and at least one tubular collar extending up from the inlet opening, which fits over the cylindrical tube of the canister for delivering waste material from the cuspidor.

5. The filter assembly of claim 4, wherein the tubular collar includes a stop comprising an internal diameter reduction positioned for engagement by an upper end of the cylindrical tube, thereby holding the filter basket at an elevated position within the interior chamber of the canister.

6. The filter canister assembly of claim 1, wherein the filter closure is secured to the side walls of the filter basket by a snap fit means engaged when the filter closure is pushed tightly onto the side walls of the filter basket.

7. The filter canister assembly of claim 1, wherein the filter closure is permanently secured to the side walls of the filter basket.

8. The filter canister assembly of claim 7, wherein the filter closure is secured to the side walls of the filter basket by heat bonding.

9. The filter canister assembly of claim 7, wherein the filter closure is secured to the side walls of the filter basket by permanent adhesive.

\* \* \* \* \*